US005628930A

United States Patent [19]

Weers et al.

[11] Patent Number: 5,628,930

[45] Date of Patent: May 13, 1997

[54] STABILIZATION OF FLUOROCARBON EMULSIONS

[75] Inventors: Jeffry G. Weers, San Diego; David H. Klein, Carlsbad; Cindy S. Johnson, Oceanside, all of Calif.

[73] Assignee: Alliance Pharmaceutical Corp., San Diego, Calif.

[21] Appl. No.: 967,700

[22] Filed: Oct. 27, 1992

[51] Int. Cl.$^6$ .............................. B01J 13/00; A61K 31/02

[52] U.S. Cl. .......................... 252/312; 252/314; 514/746; 514/937; 514/743

[58] Field of Search .................................... 252/312, 314, 252/311; 514/832, 833, 743, 746, 937, 938; 424/9.37, 9.45, 9.52

[56] References Cited

U.S. PATENT DOCUMENTS

| | | | |
|---|---|---|---|
| 4,289,499 | 9/1981 | Clark, Jr. et al. | 436/16 |
| 4,613,708 | 9/1986 | Riess et al. | 514/832 X |
| 4,859,363 | 8/1989 | Davis et al. | 252/312 |
| 4,865,836 | 9/1989 | Long, Jr. | 514/832 |
| 4,866,096 | 9/1989 | Schweighardt | 514/832 |
| 4,895,876 | 1/1990 | Schweighardt | 514/747 |
| 4,987,154 | 1/1991 | Long, Jr. | 514/832 |
| 5,120,731 | 6/1992 | Meinert et al. | 514/231.5 |
| 5,171,755 | 12/1992 | Kaufman et al. | 514/832 X |
| 5,264,220 | 11/1993 | Long, Jr. et al. | 514/832 X |
| 5,393,513 | 2/1995 | Long, Jr. | 424/5 |
| 5,441,733 | 8/1995 | Meinert | 514/746 |

FOREIGN PATENT DOCUMENTS

| | | |
|---|---|---|
| 0415263 | 8/1990 | European Pat. Off. . |
| WO9301798 | 4/1993 | WIPO . |

OTHER PUBLICATIONS

Kabal'nov, et al. "Influence of Nature and Composition of Disperse Phase in Emulsions of Perfluoroorganic Compounds on the Kinetics of the Decrease in Emulsion Dispersity" *Killoidn Zh.* 48:27–32 (1986).

Kabal'nov et al. "Ostwald Ripening Theory: Applications to Fluorocarbon Emulsion Stability" *Adv. Colloid Interface Sci.,* 38:69–97 (Mar. 23, 1992).

Lifshits et al. "Kinetics of Diffusive Decomposition of Supersaturated Solid Solutions" *Sov. Phys. JEPT,* 35:331–339 (1959).

Riess, "Reassessment of Criteria for the Selection of Perfluorochemicals for Second–Generation Blood Substitutes: Analysis of Structure/Property Relationships" *Artificial Organs,* 8:44–56 (1984).

Reiss et al. "Design, Synthesis and Evaluation of Fluorocarbons and Surfactants for In Vivo Applications New Perfluoroalkylated Polyhydroxylated Surfactants" *Biomat. Artif. Cells Artif. Organs,* 16:421–430 (1988).

Davis et al. "Ostwald Ripening and the Stability of Emulsion Systems an Explanation for the Effect of an Added Third Component" *J. Colloid & Interface Sci.,* 80:508–511 (1981).

Higuchi et al. "Physical Degradation of Emulsions Via the Molecular Diffusion Route and Possible Prevention Thereof" *J. Pharm. Sci.,* 51:459–466 (1962).

Kabal'nov et al. "Application of Lifshits–Slezov Theory to Transcondensation of Oil–Water Emulsions" *Kolloidhyi Z.,* 46:1108–1111 (1984).

(List continued on next page.)

*Primary Examiner*—Richard D. Lovering

*Assistant Examiner*—Daniel S. Metzmaier

*Attorney, Agent, or Firm*—Knobbe, Martens, Olson & Bear

[57] ABSTRACT

Storage stable fluorocarbon emulsions having a continuous aqueous phase and a discontinuous fluorocarbon phase, in which the fluorocarbon phase comprises a major amount of a first fluorocarbon or fluorocarbon mixture, and a minor amount of a second fluorocarbon or fluorocarbon mixture, in which the second fluorocarbon has a molecular weight greater than that of the first fluorocarbon and the second fluorocarbon includes a lipophilic moiety in its structure, whereby the second fluorocarbon serves to promote particle size stability in the emulsion while simultaneously providing favorably short organ retention times when administered to animals in vivo.

34 Claims, 7 Drawing Sheets

0% w/w PFDB — 1% w/w PFDB — 10% w/w PFDB $d^3$ ($\mu m^3$)

0.15, 0.12, 0.09, 0.06, 0.03, 0.00

0, 1, 2, 3 time (months)

OTHER PUBLICATIONS

Kabal'nov et al. "Influence of Nature and Composition of Disperse Phase on Stability of Oil–in–Water Emulsions Against Transcondensation" *Kolloidnyi Z.*, 47:1048–1053 (1985).

Kabal'nov et al. "Influence of Nature and Composition of Disperse Phase in Emulsions of Perfluoroorganic Compounds of the Decrease in Emulsion Dispersity" *Kolloidnyi Z.*, 48:27–32 (1985).

Krafft et al. "Detrimental Effects of Excess Lecithin on the Stability of Fluorocarbon/Lecithin Emulsions", *J. Phys. Chem.*, 95:5673–5676 (Jul. 1991).

Lawson et al. "Methods for the Estimation of Vapor Pressures and Oxygen Solubilities of Fluorochemicals for Possible Application in Artificial Blood Formulation" *J. Fluorine Chem.*, 12:221–236 (1978).

Lowe et al. "Perfluorochemicals: Blood Substitutes and Beyond" *Adv. Mater* 3:87–93 (Feb. 1991).

Riess et al. "Solubility and Transport Phenomena in Perfluorochemicals Relevant to Blood Substitution and Other Biomedical Applications" *Pure & Applied Chem.*, 54:2383–2406 (1982).

Riess et al. "Fluorocarbon–Based In Vivo Oxygen Transport and Delivery Systems", *Vox Sang*, 61:225–239 (Dec. 1991).

Sharma, et al. "Physiochemical Assessment of Novel Formulations of Emulsified Perfluorocarbons" *Br. J. Pharm.*, 5 pages (Date unknown).

Yamanouchi et al. "Quantitative Structure–in Vivo Half–Life Relationships of Perfluorochemicals for Use as Oxygen Transporters" *Chem. Pharm. Bull.*, 33:1221–1231 (1985).

*DISTRIBUTION GRAPH (BY VOL.)
(k[D]=STANDARD)
(KAMACK CORR.)

| | | |
|---|---|---|
| D (MEDIAN) | 0.45 | [μm] |
| SD | 0.25 | [μm] |
| Sw | 14.093 | [m2/g] |

STABILIZATION OF FLUOROCARBON EMULSIONS

BACKGROUND OF THE INVENTION

The present invention relates to emulsions comprising highly fluorinated or perfluorinated compounds. More particularly, it relates to fluorocarbon emulsions having superior particle size stability during storage.

Fluorocarbon emulsions find uses as therapeutic and diagnostic agents. Most therapeutic uses of fluorocarbons are related to the remarkable oxygen-carrying capacity of these compounds. One commercial biomedical fluorocarbon emulsion, Fluosol (Green Cross Corp., Osaka, Japan), is presently used as a gas carrier to oxygenate the myocardium during percutaneous transluminal coronary angioplasty (R. Naito, K. Yokoyama, Technical Information Series No. 5 and 7, 1981). Fluorocarbon emulsions have also been used in diagnostic applications such as imaging. Radiopaque fluorocarbons such as perflubron (perfluorooctyl bromide or $C_8F_{17}Br$) are particularly useful for this purpose.

It is important that fluorocarbon emulsions intended for medical use exhibit particle size stability. Emulsions lacking substantial particle size stability are not suitable for long term storage, or they require storage in the frozen state. Emulsions with a short shelf life are undesirable. Storage of frozen emulsions is inconvenient. Further, frozen emulsions must be carefully thawed, reconstituted by admixing several preparations, then warmed prior to use, which is also inconvenient.

Davis et al., U.S. Pat. No. 4,859,363, disclose stabilization of perfluorodecalin emulsion compositions by mixing a minor amount of a higher boiling perfluorocarbon with the perfluorodecalin. Preferred higher boiling fluorocarbons were perfluorinated saturated polycyclic compounds, such as perfluoroperhydrofluoranthene. Others have also utilized minor amounts of higher boiling fluorocarbons to stabilize emulsions. See, e.g., Meinert, U.S. Pat. No. 5,120,731 (fluorinated morpholine and piperidine derivatives), and Kabalnov, et al., Kolloidn Zh. 48: 27–32 (1986) (F-N-methylcyclohexylpiperidine).

Davis, et al. suggested that the primary phenomenon responsible for instability of small particle size fluorocarbon emulsions was Ostwald ripening. During Ostwald ripening, an emulsion coarsens through migration of molecules of the discontinuous phase from smaller to larger droplets. See generally, Kabalnov, et al., Adv. Colloid Interface Sci. 38: 62–97 (1992). The force driving Ostwald ripening appears to be related to differences in vapor pressures that exist between separate droplets. Such a difference in vapor pressure arises because smaller droplets have higher vapor pressures than do larger droplets. However, Ostwald ripening may only proceed where the perfluorocarbon molecules are capable of migrating through the continuous phase between droplets of the discontinuous phase. The Lifshits-Slezov equation relates Ostwald ripening directly to water solubility of the discontinuous phase. See Lifshits, et al., Soy. Phys. JETP 35: 331 (1959).

It is known that addition of higher molecular weight compounds, having lower vapor pressures and lower solubility in the continuous phase, reduces such interparticle migration. This, in turn, reduces Ostwald ripening and improves particle size stability. Thus, the conventional prior art solution to the particle size stability problem is to add a certain amount (e.g., 10–30% of the fluorocarbon content) of a higher molecular weight fluorocarbon to the discontinuous phase.

Fluorocarbon emulsion particles are taken up and temporarily retained by cells of the reticuloendothelial system (RES). It is desirable to minimize this retention time. Unfortunately, when the prior art included higher molecular weight fluorocarbons in fluorocarbon emulsions, organ retention times were also increased considerably. Organ retention time for most fluorocarbons bears an exponential relationship to the molecular weight of the fluorocarbon. See J. G. Riess, Artificial Organs 8: 44, 49–51; J. G. Riess, International Symposium on Blood Substitutes, Bari, Italy: Jun. 19–20, 1987, Proceedings pp. 135–166.

There is a need for perfluorocarbon emulsions that exhibit both storage stability in the nonfrozen state and a rapid rate of elimination from the body. Accordingly, it is an object of the invention to provide fluorocarbon emulsions having these characteristics.

SUMMARY OF THE INVENTION

The present invention involves stabilization of fluorocarbon emulsions with higher molecular weight fluorocarbons that include a lipophilic moiety. Alternatively, any fluorocarbon having a critical solution temperature that is 10° C. or more below that which is predicted by its molecular weight can be used to stabilize fluorocarbon emulsions in accordance with this invention.

A major advantage of the present invention is the surprisingly short organ retention times of the stabilized emulsion. Perfluorodecyl bromide, for example, has a calculated half life in vivo in organs of the reticuloendothelial system (RES) of approximately 18 days, while those of nonlipophilic perfluorocarbons having about the same molecular weight vary from about 50 to 300 days. (See Table IV.) This distinction is critical; it spells the difference between formulations which are physiologically acceptable and those which are not. Note that none of the prior art stabilizers are lipophilic; thus, none share the advantageous properties of the present invention. For example, with reference to Table IV and FIG. 5, the stabilizers of the present invention all have critical solution temperatures (CSTs) and projected organ retention times much lower than those of the prior art stabilizers of Davis, et al., Kabalnov, and Meinert. Aside from the stabilizers of the present invention, conventional fluorocarbons exhibit a direct correlation between retention time in RES organs and molecular weight. Also, aside from the lipophilic fluorocarbons used in the present invention, the perfluorochemical structure has little effect on the strong retention time/molecular weight relationship. Thus, the presence of heteroatoms or cyclic structure has little effect on organ retention time.

Another major advantage of the present invention over the prior art is that the emulsions are remarkably stable. This is particularly true when both the major (first) fluorocarbon and the stabilizing (second) fluorocarbon include lipophilic moieties.

Thus, in accordance with one aspect of the present invention, there is provided a storage stable fluorocarbon emulsion, comprising a continuous aqueous phase, an effective amount of an emulsifying agent, and a discontinuous fluorocarbon phase, comprising from about 50% to about 99.9% of a one or more first fluorocarbons, and from about 0.1% to about 50% of one or more second fluorocarbons having a molecular weight greater than each such first fluorocarbon, wherein each such second fluorocarbon includes at least one lipophilic moiety. The first fluorocarbon can be selected from a variety of materials, including his (F-alkyl) ethenes, perfluoroethers having the general structure $C_nF_{2n+1}$—O—$C_{n'}F_{2n'+1}$, wherein the sum of n and n' equals 6 to 8, perfluoromethylbicyclo [3.3.1]-nonane, perfluoro-2,2,4,4-tetramethylpentane, perfluorotripropylamine, bis(F-butyl)ethene, (F-isopropyl) (F-hexyl) ethene, perfluoromethyladamantane, perfluorodimethyladamantane, F-N-methyldecahydroisoquinoline, F-4-methyloctahydroquinolidizine, perfluorodecalin, or most preferably, perfluorooctyl bromide. In one embodiment, each first fluorocarbon has a molecular weight from about 460 Daltons to about 550 Daltons, and also preferably has a half life in vivo of less than about 4 weeks, preferably less than 2 or 3 weeks, and most preferably 7 days or less. In the second fluorocarbon, the lipophilic moiety or moities are advantageously Br, Cl, I, H, $CH_3$, or a saturated or unsaturated hydrocarbon chain of 2 or 3 carbon atoms. In one preferred embodiment, the second fluorocarbon is an aliphatic perfluorocarbon having the general formula $C_nF_{2n+1}R$ or $C_nF_{2n}R_2$, wherein n is an integer from 9 to 12 and R is the lipophilic moiety. In various preferred embodiments, the second fluorocarbon is selected from the group consisting of perfluorododecyl bromide, $C_{10}F_{21}CH{=}CH_2$, or $C_{10}F_{21}CH_2CH_3$, or linear or branched brominated perfluorinated alkyl ethers. Most preferably, the second fluorocarbon comprises perfluorodecyl bromide. It is desirable that each second fluorocarbon has a molecular weight greater than about 550 Daltons. Pursuant to an alternative definition of the second fluorocarbon, each second fluorocarbon has a critical solution temperature in hexane at least 10° C. lower than that of a fully fluorinated fluorocarbon having substantially the same molecular weight (i.e., a molecular weight within 10, and preferably within 3, 4, or 5 daltons). In preferred emulsions, the discontinuous fluorocarbon phase comprises from about 60% to about 99.5% of the first fluorocarbon, and from about 0.5% to about 40% of the second fluorocarbon; more preferably from about 80% to about 99% of the first fluorocarbon, and from about 1% to about 20% of the second fluorocarbon. A particularly preferred emulsifier is egg yolk phospholipid, and preferred amounts of this emulsifier are 1%–10% w/v. Also preferred are the fluorinated surfactants.

Another aspect of the present invention comprises a method for imparting particle size stability to a fluorocarbon emulsion having a discontinuous phase of one or more first fluorocarbons and a continuous aqueous phase, comprising the step of including in admixture with said first fluorocarbon an emulsion-stabilizing amount of one or more second fluorocarbons having a molecular weight greater than said first fluorocarbon, wherein each said second fluorocarbon includes within its structure a lipophilic moiety. In this method, the definitions of the first and second fluorocarbons, the surfactant, and the various emulsion parameters can be the same as for the emulsions discussed.

DESCRIPTION OF THE PREFERRED EMBODIMENTS

I. Introduction

Figure 1:
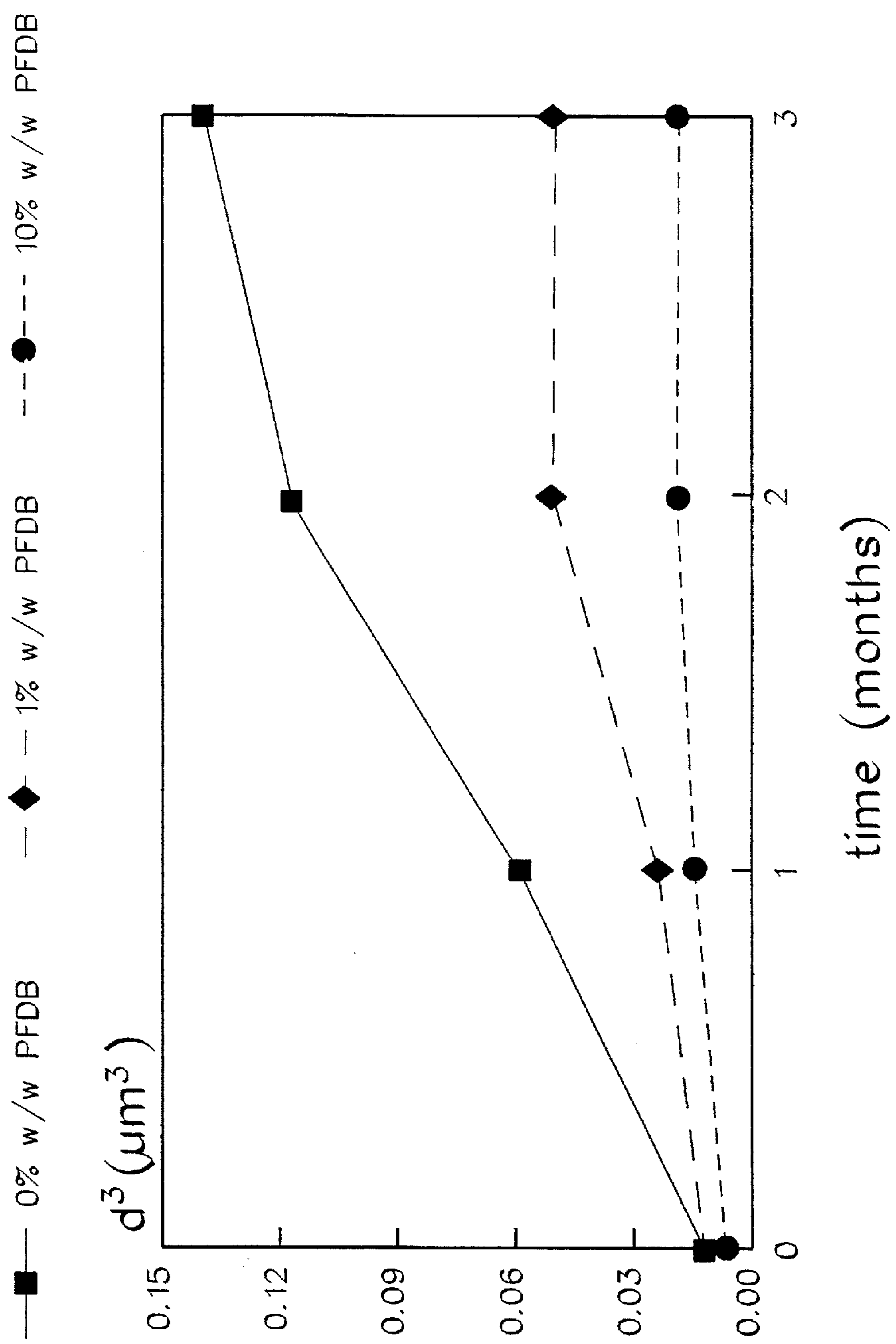
FIG. 1 represents accelerated stability testing (T=40° C.) for 90% w/v fluorocarbon, 4% w/v egg yolk phospholipid emulsions containing mixtures of perfluorooctyl bromide and perfluorodecyl bromide. The stability of emulsions with 0%, 1%, and 10% w/w perfluorodecyl bromide are presented in plots of diameter cubed ($\mu m^3$) vs. time (months).

The fluorocarbon emulsions of the present invention comprise two phases: a continuous aqueous phase and a discontinuous fluorocarbon phase. Osmotic agents and buffers, generally, are also included in the continuous phase to maintain osmolarity and pH to promote physiological acceptability.

The discontinuous phase of modern fluorocarbon emulsions for therapeutic use generally comprises from 20% w/v to up to 125% w/v of a fluorocarbon or a highly fluorinated compound (hereinafter referred as a "fluorocarbon" or a "perfluorocarbon"). As used herein, the expression "weight per volume" or "w/v" will mean grams per 100 cubic centimeters or milliliters. Also, as used herein, the expression "weight per weight" or "w/w" will be used and understood to mean the weight fractions of components that add up to give a desired weight per volume.

The present invention provides stable fluorocarbon emulsions by forming the discontinuous phase from a mixture of at least two fluorocarbons, at least one of which has a relatively higher molecular weight and which includes in its molecular structure a lipophilic moiety. Unlike prior art emulsions in which a higher molecular weight fluorocarbon is included to prevent Ostwald ripening, the present added fluorocarbon(s) are excreted at a rate which is physiologically acceptable. Stable fluorocarbon emulsions with particle sizes as small as ca. 0.1 μm may be prepared, with good particle size stability. Surprisingly, emulsions of the present invention may be stored with little or no particle growth at relatively elevated temperatures of 20° C. to 40° C.

A preferred embodiment utilizes two fluorocarbons; however, the "first" and "second" fluorocarbons discussed below can instead comprise mixtures of fluorocarbons, each of which has the specified characteristics.

The first fluorocarbon preferably has a molecular weight from about 460 to 550 Daltons and is employed in a relative ratio of 50% to 99.9% by weight. The second fluorocarbon is preferably an aliphatic fluorocarbon, including within its molecular structure at least one lipophilic moiety, and having a molecular weight greater than about 550 Daltons at a relative ratio of 50% to 0.1%. Linear fluorocarbons are preferred for both the first and second fluorocarbons. The second fluorocarbon is preferably terminally substituted with the lipophilic moiety, although substitutions at other positions are also contemplated.

A first alternative definition of the second fluorocarbon focuses on its critical solution temperature (CST). In accordance with this definition, the second fluorocarbon has a CST that is lower than the CST of a fully fluorinated fluorocarbon (lacking a lipophilic moiety) having substantially the same molecular weight. Preferably, the CST of the second fluorocarbon is at least 10° lower than such a fully fluorinated fluorocarbon.

A second alternative definition of the second fluorocarbon focuses on its organ retention time. It is possible to predict organ retention time from a log plot of the molecular weight of the fluorocarbon. In the present invention, the second fluorocarbon preferably has an organ retention time that is less than what is predicted by the aforementioned log plot.

Emulsions may be prepared through the method of the present invention at very high fluorocarbon concentrations (up to 125%, w/v), virtually any desired particle size, and with very low quantities of emulsifying agents, without losing stability. Unlike prior art, stabilized fluorocarbon emulsions, the organ retention time of the added fluorocarbon is well within acceptable limits. Further advantages and attributes are discussed below.

II. The Compositions

A. The Discontinuous Phase

The characteristics of fluorocarbons suitable for use in the present invention are discussed in more detail below. Examples of suitable fluorocarbons are provided.

1. The First Fluorocarbon

The first fluorocarbon is selected for its short organ retention time and biocompatibility. In general, the half life in organs is preferably less than about 4 weeks, more preferably less than about 2 or 3 weeks, and most preferably 7 days or less. The molecular weight is from about 460 to about 550 daltons.

Such fluorocarbons include bis(F-alkyl)ethenes such as $C_4F_9CH{=}CHC_4F_9$ ("F-44E"), i-$CF_3CF_9CH{=}CHC_6F_{13}$ ("F-i36E"), and cyclic fluorocarbons, such as $C_{10}F_{18}$ (F-decalin, perfluorodecalin or FDC); F-adamantane (FA); perfluoroindane; F-methyladamantane (FMA); F-1,3-dimethyladamantane (FDMA); perfluoro-2,2,4,4-tetramethylpentane; F-di- or F-trimethylbicyclo[3,3,1] nonane (nonane); $C_{7-12}$ perfluorinated amines, such as F-tripropylamine, F-4-methyloctahydroquinolizine (FMOQ), F-n-methyldecahydroisoquinoline (FMIQ), F-n-methyldecahydroquinoline (FHQ), F-n-cyclohexylpyrrolidine (FCHP), and F-2-butyltetrahydrofuran (FC-75 or RM101).

Other examples of appropriate first fluorocarbons include brominated perfluorocarbons, such as perfluorooctyl bromide ($C_8F_{17}Br$, USAN perflubron), 1-bromopentadecafluoroheptane ($C_7F_{15}Br$), and 1-bromotridecafluorohexane ($C_6F_{13}Br$, also known as perfluorohexyl bromide or PFHB. Other brominated fluorocarbons are disclosed in U.S. Pat. Nos. 3,975,512 and 4,987,154 to Long.

Also contemplated are fluorocarbons having other non-fluorine substituents, such as 1-chloroheptadecafluorooctane ($C_8F_{17}Cl$, also referred to as perfluorooctyl chloride or PFOCl); perfluorooctyl hydride, and similar compounds having different numbers of carbon atoms.

Additional first fluorocarbons contemplated in accordance with this invention include perfluoroalkylated ethers, halogenated ethers (especially brominated ethers), or polyethers, such as $(CF_3)_2CFO(CF_2CF_2)_2OCF(CF_3)_2$; $(C_4F_9)_2O$. Further, fluorocarbon-hydrocarbon compounds may be used, such as, for example compounds having the general formula $C_nF_{2n+1}C_{n'}H_{2n'+1}$; $C_nF_{2n+1}OC_{n'}H_{2n'+1}$; or $C_nF_{2n+1}CH{=}CHC_{n'}H_{2n'+1}$, wherein n and n' are the same or different and are from about 1 to about 10 (so long as the compound is a liquid at room temperature). Such compounds, for example, include $C_8F_{17}C_2H_5$ and $C_6F_{13}CH{=}CHC_6H_{13}$.

Particularly preferred fluorocarbons for use as the first fluorocarbon include perfluoroamines, terminally substituted linear aliphatic perfluorocarbons having the general structure:

$C_nF_{2n+1}R$, wherein n is an integer from 6 to 8 and R comprises a lipophilic moiety selected from the group of Br, Cl, I, $CH_3$, or a saturated or unsaturated hydrocarbon of 2 or 3 carbon atoms, bis (F-alkyl) ethenes having the general structure:

$C_nF_{2n+1}$—CH=CH—$C_{n'}F_{2n'+1}$, wherein the sum of n and n' equals 6 to 10, and perfluoroethers having the general structure:

$C_nF_{2n+1}$—O—$C_{n'}F_{2n'+1}$, wherein the sum of n and n' equals 6 to 10.

In addition, fluorocarbons selected from the general groups of perfluorocycloalkanes or perfluoroalkylcycloalkanes, perfluoroalkyl saturated heterocyclic compounds, or perfluorotertiary amines may be suitably utilized as the first fluorocarbon. See generally Schweighart, U.S. Pat. No. 4,866,096.

It will be appreciated that esters, thioethers, and other variously modified mixed fluorocarbon-hydrocarbon compounds, including isomers, are also encompassed within the broad definition of fluorocarbon materials suitable for use as the first fluorocarbon of the present invention. Other suitable mixtures of fluorocarbons are also contemplated.

Additional fluorocarbons not listed here, but having the properties described in this disclosure that would lend themselves to therapeutic applications, are also contemplated. Such fluorocarbons may be commercially available or specially prepared. As will be appreciated by one skilled in the art, there exist a variety of methods for the preparation of fluorocarbons that are well known in the art. See for example, Schweighart, U.S. Pat. No. 4,895,876.

2. The Second Fluorocarbon

The second fluorocarbon is an aliphatic fluorocarbon substituted with one or more lipophilic moieties and having a higher molecular weight than the first fluorocarbon. Advantageously, the lipophilic moiety is a terminal substitution on the fluorocarbon molecule. Preferably, the molecular weight of the second fluorocarbon is greater than about 540 Daltons. Constraints on the upper limit of the molecular weight of the second fluorocarbon will generally be related to its organ retention time and its ability to be solubilized by the first fluorocarbon. Usually, the second fluorocarbon has a molecular weight less than about 700 Daltons.

Most preferred second fluorocarbons have boiling points greater than about 150° C. and water solubilities of less than about $1\times10^{-9}$ moles/liter.

Of course, as will be appreciated by one skilled in the art, many fluorocarbons substituted with different lipophilic groups could be suitably used as the second fluorocarbon in the present invention. Such fluorocarbons may include esters, thioethers, and various fluorocarbon-hydrocarbon compounds, including isomers. Mixtures of two or more fluorocarbons satisfying the criteria set forth herein are also encompassed within the broad definition of fluorocarbon materials suitable for use as the second fluorocarbon of the present invention. Fluorocarbons not listed here, but having the properties described in this disclosure that would lend themselves to therapeutic applications are additionally contemplated.

The lipophilic moiety is optimally selected from the group consisting of Br, Cl, I, $CH_3$, or a saturated or unsaturated hydrocarbon of 2 or 3 carbon atoms. Consequently, preferred second fluorocarbons may be selected from the group of terminally substituted perfluorocarbon halides as represented by the general formula:

$C_nF_{2n+1}X$ or $C_nF_{2n}X_2$, wherein n is 8 or greater, preferably 10 to 12, and X is a halide selected from the group consisting of Br, Cl, or I;

1-alkyl-perfluorocarbons or dialkylperfluorocarbons as represented by the general formula:

$C_nF_{2n+1}$—$(CH_2)_{n'}CH_3$ wherein n is 8 or greater, preferably 10 to 12, and n' is 0 to 2;

1-alkenyl-perfluorocarbons as represented by the general formula:

$C_nF_{2n+1}$—$C_{n'}H_{(2n'-1}$, wherein n is 10 or more, preferably 10 to 12, and n' is either 2 or 3; or brominated linear or branched perfluoroethers or polyethers having the following general structure:

Br—$(C_nF_{2n+1}$—O—$C_{n'}F_{2n'+1})$, wherein n and n' are each at least 2 and the sum of n and n' is greater than or equal to 8.

Most preferably, the second fluorocarbon of the present invention is selected from the group consisting of linear or branched brominated perfluorinated alkyl ethers, perfluorodecyl bromide ($C_{10}F_{21}Br$); perfluorododecyl bromide ($C_{12}F_{25}Br$); 1-perfluorodecylethene ($C_{10}F_{21}CH{=}CH_2$); and 1-perfluorodecylethane ($C_{10}F_{21}CH_2CH_3$); with perfluorodecyl bromide particularly preferred.

In accordance with a first alternative definition, whether or not they satisfy the foregoing definitions, fluorocarbons having critical solution temperatures (CSTs) vs hexane more than 10° C. below the CST of a fluorocarbon having substantially the same molecular weight (variations of up to about 10 daltons being acceptable) are also suitable for use in the present invention. A comparison between the CST and molecular weight of a number of perfluorocarbons is presented in Table IV, below. Methodology for determining CST is presented in Example 9.

Figure 6:
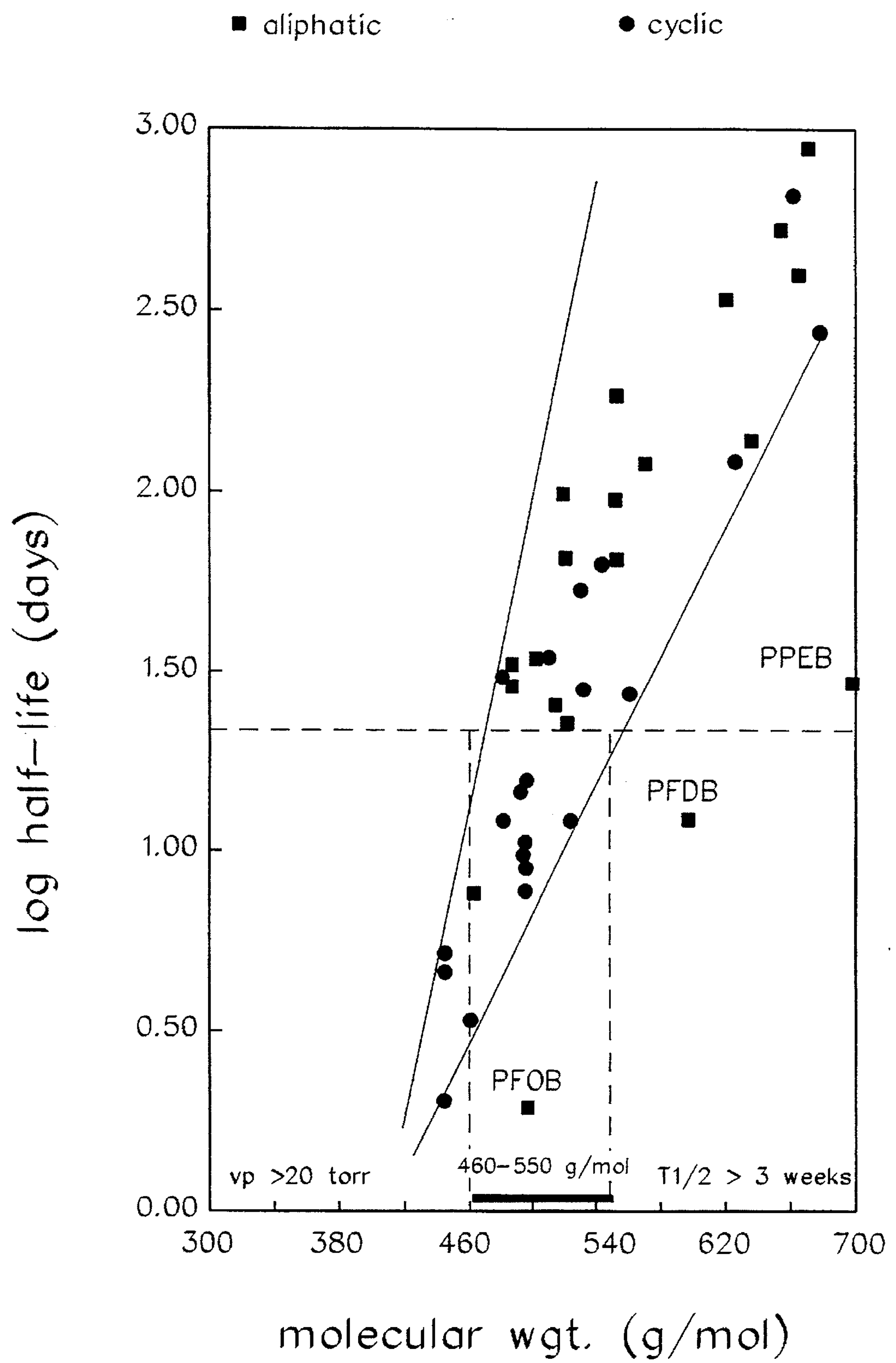
FIG. 6 is a plot of the organ half-life in days vs. molecular weight of the fluorocarbon in g/mol. Traditionally, the molecular weight region from 460–550 g/mol has been considered optimal for blood substitute applications. The lower cutoff is related to the formation of gas emboli for fluorocarbons with vapor pressures greater than 20 torr. The upper cutoff is limited to compounds with organ retention times of less than 3 weeks. It is clear that the lipophilic compounds do not fit the general trend in that they have shorter organ retention times than would be predicted for their molecular weight. PFDB has a half-life less than the prescribed 3 week cutoff. (Note—because the organ half-life depends on dose and method of measurement, the values for PFOB and PFDB have been scaled relative to F-decalin knowing that the ratio of half-lives for PFOB/FDC=4/7).

A second alternative definition of the second fluorocarbon is evident from FIG. 6 and Example 8. Suitable second fluorocarbons may be selected from those which have significantly lower half lives than nonlipophilic fluorocarbons of substantially the same molecular weight. As is evidenced in FIG. 6, the log of the half life in days of suitable second fluorocarbons can be at least 0.2, preferably at least 0.3, and more preferably at least 0.4 or 0.5 less than the average or expected value for nonlipophilic fluorocarbons of substantially the same molecular weight.

3. The Emulsifying Agent

The fluorocarbon emulsions also include an emulsifying agent. As used in this specification, an emulsifying agent is any compound or composition that aids in the formation and maintenance of the droplets of the discontinuous phase by forming a layer at the interface between the discontinuous and continuous phases. The emulsifying agent may comprise a single compound or any combination of compounds, such as in the case of co-surfactants.

In the present invention, preferred emulsifying agents are selected from the group consisting of phospholipids, nonionic surfactants, fluorinated surfactants, which can be neutral or anionic, and combinations of such emulsifying agents.

Lecithin is a phospholipid that has frequently been used as a fluorocarbon emulsifying agent, as is more fully described in U.S. Pat. No. 4,865,836. Egg yolk phospholipids have shown great promise as emulsifying agents for fluorocarbons. See e.g., Long, U.S. Pat. No. 4,987,154.

Other emulsifying agents may be used with good effect, such as fluorinated surfactants, also known as fluorosurfactants. Fluorosurfactants that can provide stable emulsions include triperfluoroalkylcholate; perfluoroalkylcholestanol; perfluoroalkyloxymethylcholate; $C_3F_7O(CF_2)_3C({=}O)NH(CH_2)_3N(O)(CH_3)_2$ (XMO-10); and fluorinated polyhydroxylated surfactants, such as, for example, those discussed in "Design, Synthesis and Evaluation of Fluorocarbons and Surfactants for In Vivo Applications New Perfluoroalkylated Polyhydroxylated Surfactants" by J. G. Riess, et al. J. G. Riess et al.,; Biomat. Artif. Cells Artif. Organs 16: 421–430 (1988).

The nonionic surfactants suitable for use in the present invention include polyoxyethylene-polyoxypropylene copolymers. An example of such class of compounds is Pluronic, such as Pluronic F-68. Anionic surfactants, particularly fatty acids (or their salts) having 12 to 24 carbon atoms, may also be used. One example of a suitable anionic surfactant is oleic acid, or its salt, sodium oleate.

It will be appreciated that choice of a particular emulsifying agent is not central to the present invention. Indeed, virtually any emulsifying agent (including those still to be developed) capable of facilitating formation of a fluorocarbon-in-water emulsion can form improved emulsions when used in the present invention. The optimum emulsifying agent or combination of emulsifying agents for a given application may be determined through empirical studies that do not require undue experimentation. Consequently, one practicing the art of the present invention should choose the emulsifying agent or combination of emulsifying agents for such properties as biocompatibility.

B. The Continuous Phase

The continuous phase comprises an aqueous medium. Preferably, the medium is physiologically acceptable. For instance, a preferred emulsion will have the ability to buffer and maintain pH, as well as provide an appropriate osmolarity. This typically has been achieved in the art through the inclusion in the aqueous phase of one or more conventional buffering and/or osmotic agents, or an agent that combines these properties.

Additionally, one may supplement the continuous phase with other agents or adjuvants for stabilizing or otherwise increasing the beneficial aspects of the emulsion. These agents or adjuvants include: steroid hormones, cholesterol, tocopherols, and/or mixtures or combinations thereof. Suitable steroid hormones include fluorinated corticosteroids.

C. Preparation of the Emulsion

Fluorocarbon emulsions according to the invention are prepared by means of conventional emulsification procedures, such as, for example, mechanical or ultrasonic emulsification of an emulsion formulation in a Manton-Gaulin mixer or Microfluidizer (Microfluidics Corp., Newton, Mass.) as described in Example 1.

The first and second fluorocarbons are combined with the aqueous phase in the desired ratios, together with the surfactant. Usually, a preemulsion mixture is prepared by simple mixing or blending of the various components. This preemulsion is then emulsified in the desired emulsification apparatus.

The second fluorocarbon can comprise from about 0.1% to 50% (w/w) of the total amount of fluorocarbon; in preferred embodiments, the second fluorocarbon comprises from about 0.5% to about 40% of the total amount of fluorocarbon, with the first fluorocarbon comprising the remainder of the total fluorocarbon. The combined fluorocarbon concentration in the emulsion is preferably anywhere within the range of about 20% to about 125% (w/v). In preferred emulsions, the total perfluorocarbon concentration is from about 30%, 40%, or 50% to about 70%, 80%, 90%, or 100% (w/v). Emulsifiers are added in concentrations of from about 0.1% to 10%, more preferably 1% or 2% to about 6% (w/v).

4. Effect of Stabilizer on Emulsion Particle Size

Figure 2A:
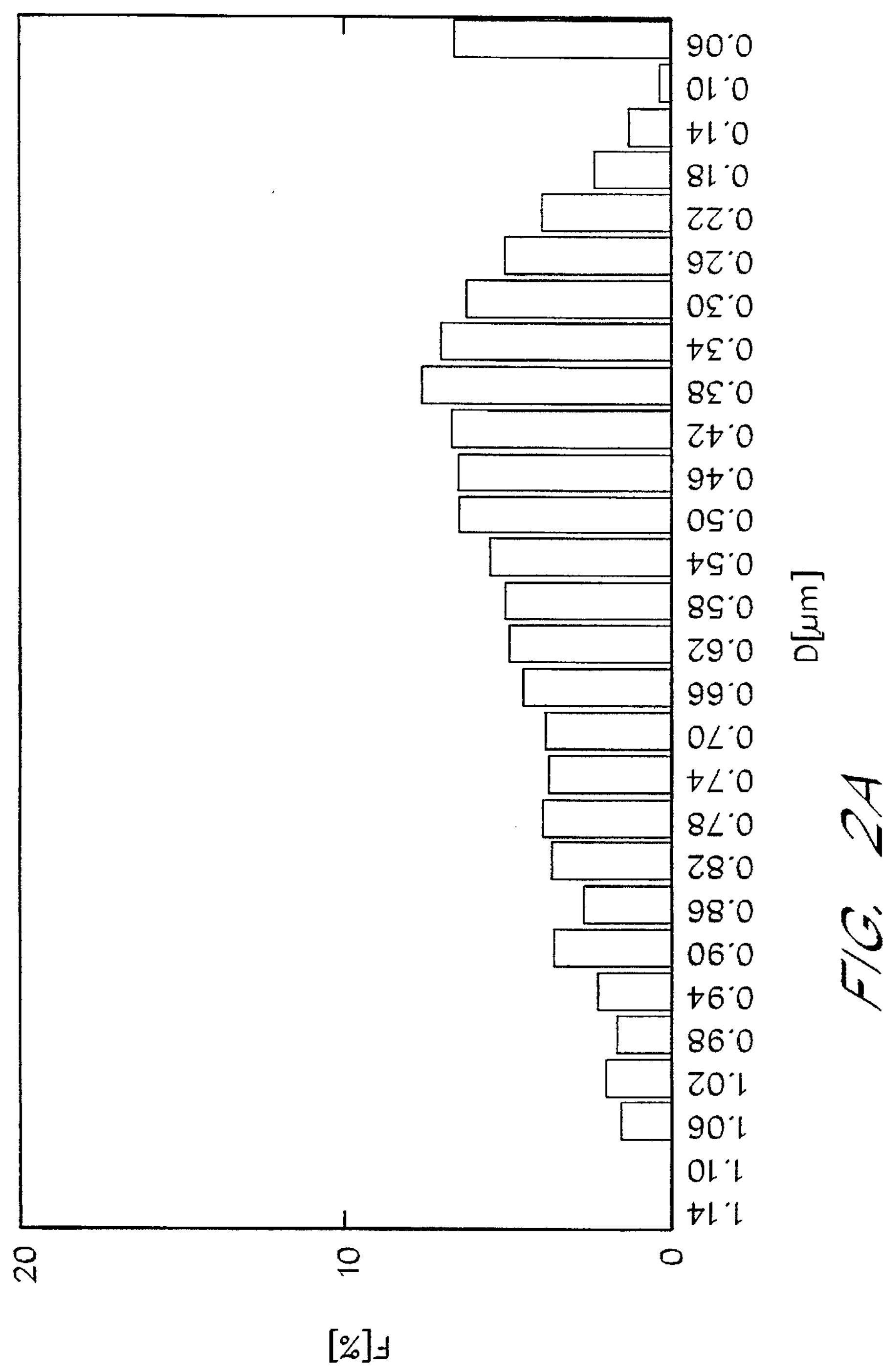
FIGS. 2A and 2B represent particle size histograms (as obtained by photosedimentation) after three months storage at 40° C. for a 90% w/v fluorocarbon emulsion containing 95/5% w/w mixture of perfluorooctyl bromide to perfluorodecyl bromide prepared under similar conditions to those of FIG. 1. The emulsions are stabilized by 4% w/v egg yolk phospholipid. (Note the emulsion particle diameters as reported on the Figures are not corrected for the vesicle fraction which shows up as a peak in the first histogram bar).
Figure 2B:
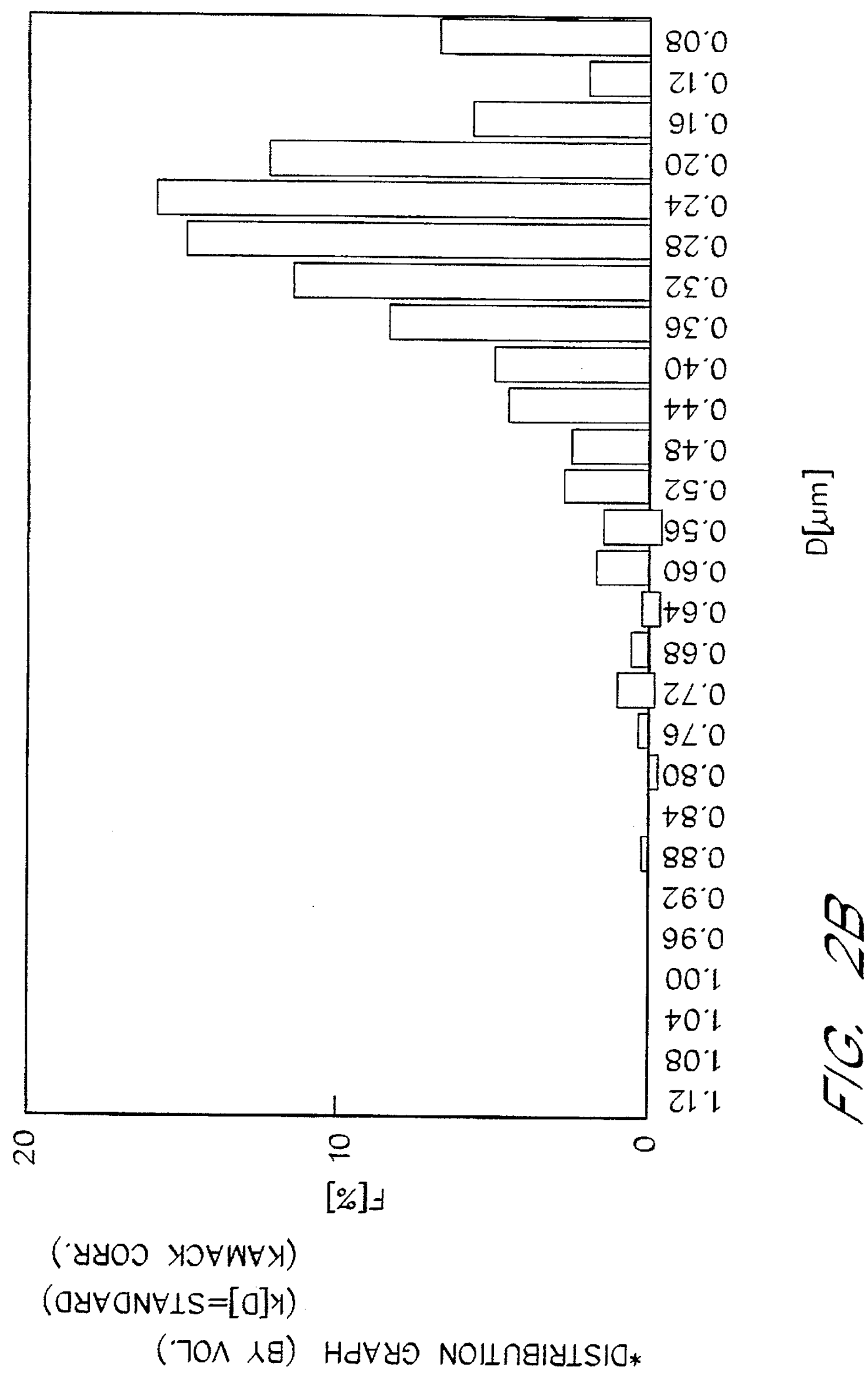

The addition of stabilizing second fluorocarbons such as perfluorodecyl bromide to 90% perfluorocarbon emulsion comprising perfluorooctyl bromide provides substantial decreases in the range of particle size and improves particle size stability (Example 3, Table 1). The data in FIG. 1 representing average particle growth size in 90% w/v perfluorocarbon emulsions containing 1% and 10% perfluorodecyl bromide (PFDB) indicate that the stabilizing effect of PFDB on particle size can be observed in emulsion comprising only 1% w/w PFDB, and that substantial improvement occurs at the 10% w/w concentration level. The data of FIG. 2 indicate that PFDB at an intermediate concentration of 4.5% w/v (equivalent to 5% w/w of total perfluorocarbon) also maintains a narrower distribution of particle sizes in a 90% w/v perfluorocarbon emulsion after 3 months of aging as compared to a non-stabilized emulsion. Perflubron emulsions stabilized with PFDB also have smaller initial particle sizes (Tables I and II, FIG. 2).

Figure 3:
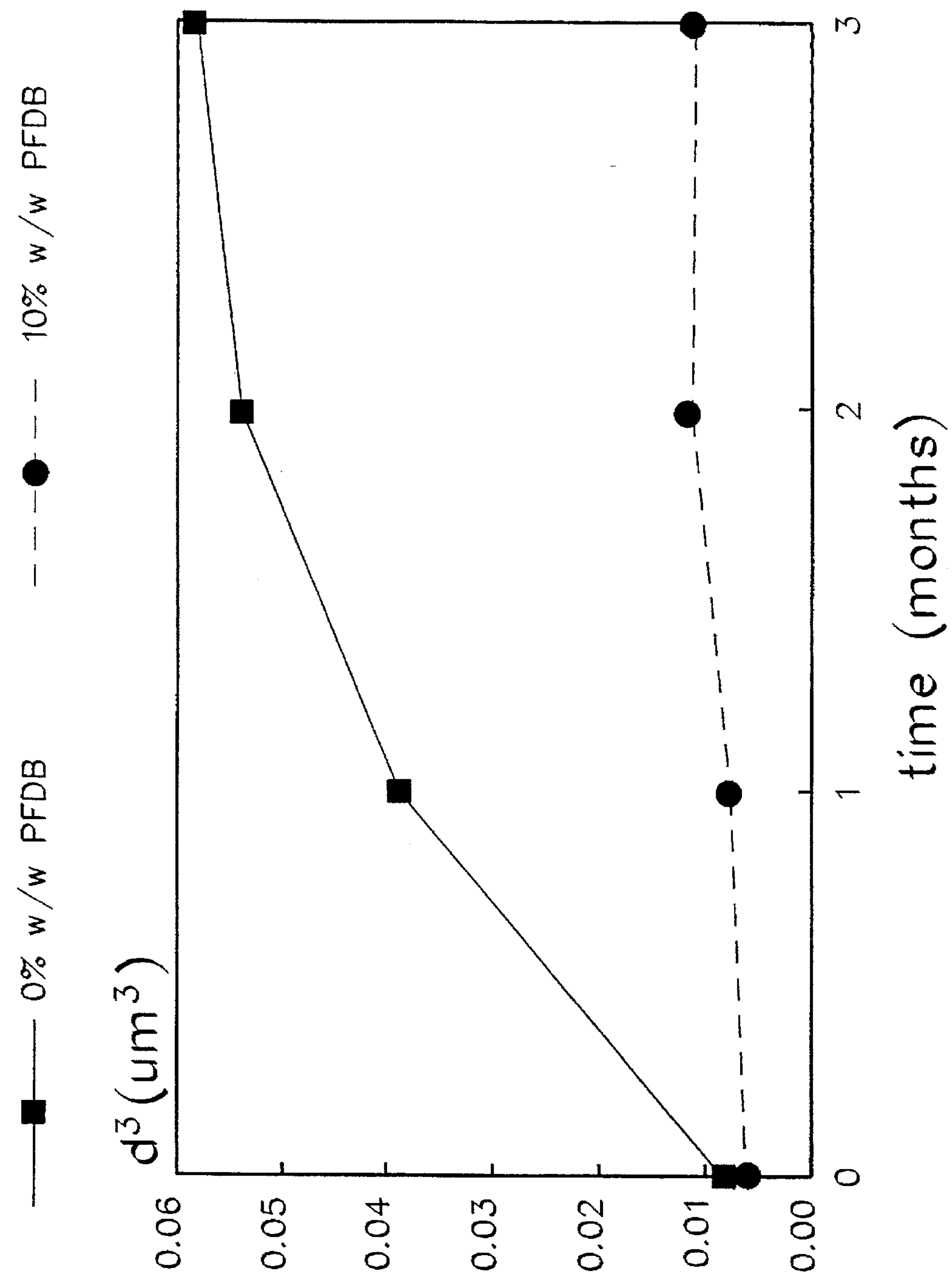
FIG. 3 represents accelerated stability testing (T=40° C.) for 60% w/v fluorocarbon, 4% w/v egg yolk phospholipid emulsions containing mixtures of perfluorooctyl bromide and perfluorodecyl bromide. The stability of emulsions with 0% and 10% w/w perfluorodecyl bromide are presented in plots of diameter cubed ($\mu m^3$) vs. time (months).

The stabilizing effect of PFDB in perfluorocarbon emulsion is also independent of total fluorocarbon concentration (Table II, FIG. 3). Emulsions comprising 60% w/v or 90% w/v perfluorocarbon, consisting of 10% w/w PFDB and 90% w/w perflubron, demonstrated similar initial average particle sizes and particle size stability on aging. The stabilizing effect of PFDB also operates in perfluorodecalin emulsions (Example 6, Table III), to produce emulsions having a small initial particle size and to substantially retain that size during three months of aging at 40° C.

The stabilizing effect of PFDB operates in both perflubron and perfluorodecalin emulsions (Example 7) comprising either 60% or 90% (Table IV) to produce emulsions having a small initial average particle size and to retain that size and substantially retaining that size during 3 months of aging at 40° C.

Further details of the method of the present invention can be more completely understood by reference to the following illustrative Examples.

EXAMPLE 1

Preparation of Reference Emulsion

Composition of Reference Emulsion: Perflubron/Lecithin (90/4% w/v)

A reference emulsion containing 90 g PFOB, 4 g egg yolk phospholipid (EYP), and physiological levels of salts and buffers was prepared by high pressure homogenization according to the method of Long (U.S. Pat. No. 4,987,154).

EXAMPLE 2

Stabilization of a 90% w/v Fluorocarbon Emulsion (Perfluorooctyl Bromide/Perfluorodecyl Bromide)

The protocol of Example 1 was repeated to form four additional emulsions, except that in successive emulsions, the fluorocarbon was perfluorooctyl bromide containing 1%, 2%, 5%, and 10% perfluorodecyl bromide (w/w), respectively.

EXAMPLE 3

Emulsion Stability

The emulsions prepared by the procedures of Examples 1 and 2 were placed on accelerated stability testing at 40° C. for three months. Table I demonstrates particle size stability over time for 90% (w/v) fluorocarbon emulsions. Such emulsions include a control, in which 100% of the fluorocarbon phase is perfluorooctyl bromide, and emulsions of the present invention in which the fluorocarbon phase is 99% to 90% w/w perfluorooctyl bromide, with from 1% to 10% w/w of perfluorodecyl bromide added as a stabilizer. In FIG. 1 and Table I, "EYP" is egg yolk phospholipid, "perflubron" is perfluorooctyl bromide, "PFDB" is perfluorodecyl bromide, and "S" is the rate of particle growth in units of $\mu m^3$/mo. FIG. 1 illustrates typical Lifshitz-Slezov graphs of $d^3$ as a function of time for these emulsions. The cubed term is chosen for the ordinate since Lifshits-Slezov theory predicts that plots of $d^3$ vs time will yield a straight line. In fact, this linear dependence is generally observed for fluorocarbon emulsions.

TABLE I

Stabilizing Effect of Perfluorodecyl bromide (90% w/v Emulsion Containing Perflubron/Perfluorodecyl bromide (PFDB) with 4% EYP, T = 40° C.)

| PFDB % w/w | Initial Size (μm) | Size After One Month | Size After Two Months | Size After Three Months | S × 1000 |
|---|---|---|---|---|---|
| 0% | 0.23 (0.13) | 0.39 (0.19) | 0.49 (0.20) | 0.52 (0.23) | 44.4 |
| 1% | 0.23 (0.12) | 0.29 (0.16) | 0.37 (0.19) | 0.37 (0.18) | 14.2 |
| 2% | 0.19 (0.09) | 0.23 (0.12) | 0.26 (0.14) | 0.32 (0.17) | 8.3 |
| 5% | 0.18 (0.08) | 0.20 (0.10) | 0.24 (0.13) | 0.28 (0.14) | 5.4 |
| 10% | 0.20 (0.12) | 0.25 (0.13) | 0.27 (0.14) | 0.27 (0.16) | 3.9 |

(parentheses indicate the standard deviation in the distribution of particle sizes)

EXAMPLE 4

Stabilization of a 60% w/v Fluorocarbon Emulsion (Perfluoroctyl Bromide/Perfluorodecyl Bromide)

Table II compares particle size increase in a 60% w/v perflubron emulsion containing perfluorodecyl bromide with a particle size increase in a reference emulsion that does not contain PFDB.

TABLE II

| Stabilization of a 60% w/v Fluorocarbon Emulsion (Perfluoroctyl Bromide/Perfluorodecyl Bromide) | | | | | |
|---|---|---|---|---|---|
| Sample | Initial Size (μm) | Size after 1 month (40° C.) | Size after 2 months (40° C.) | Size after 3 months (40° C.) | S × 1000 ($\mu m^3$/mo) |
| 0% w/v PFDB | 0.20 | 0.34 | 0.38 | 0.39 | 16.9 |
| 10% w/v PFDB | 0.18 | 0.20 | 0.23 | 0.23 | 2.3 |

EXAMPLE 5

In Vivo Data

Figure 4:
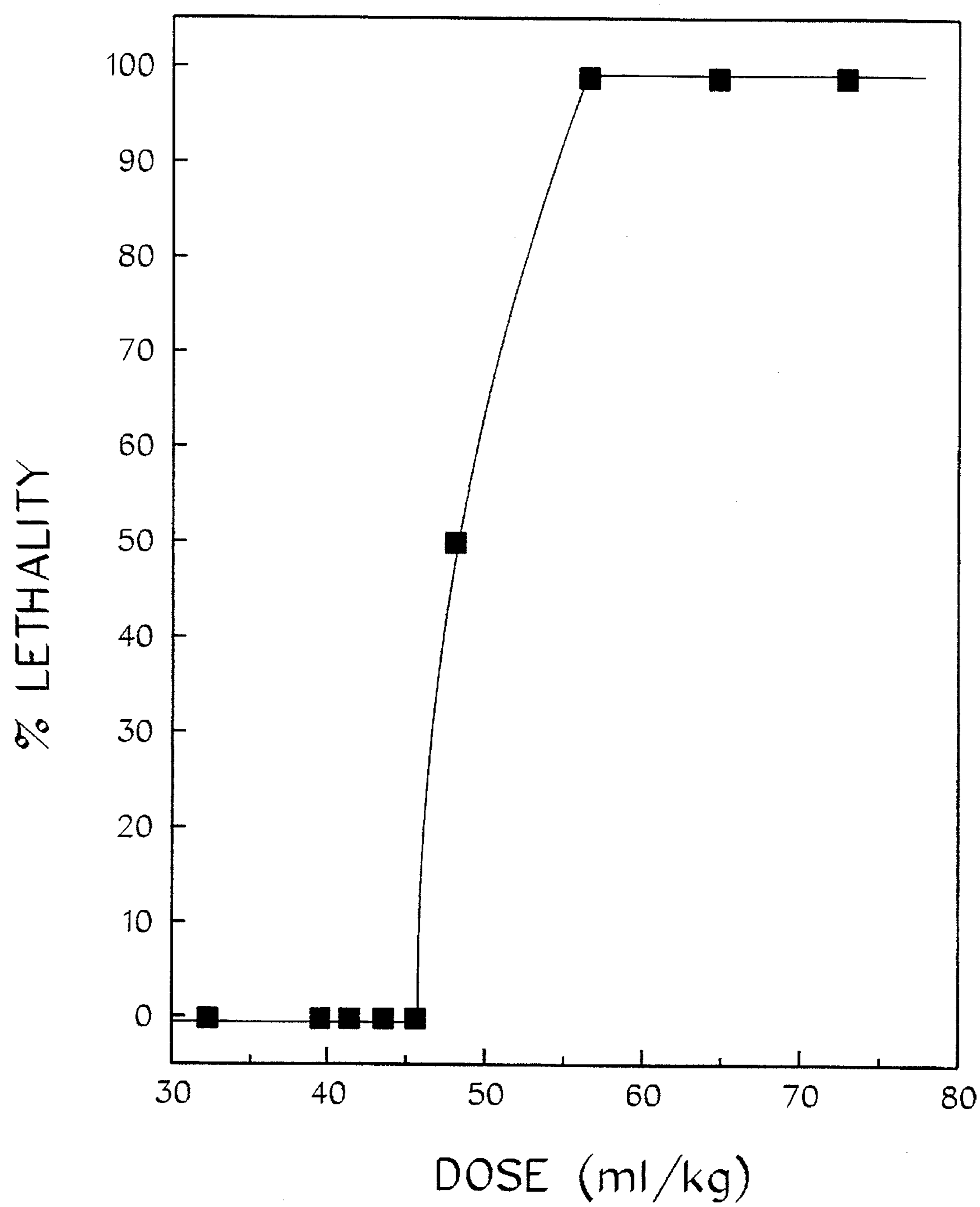
FIG. 4 represents a plot of percent mouse lethality vs. dose (ml/kg) for a 3% egg yolk phospholipid, 90% w/v fluorocarbon emulsion containing 90%/10% w/w perfluorooctyl bromide/perfluorodecyl bromide. The $LD_{50}$ of this emulsion is approximately 48 ml/kg.

FIG. 4 graphs the $LD_{50}$ in mice of a 90% w/v perfluorocarbon emulsion of the present invention, consisting of 90% w/w Perflubron, as the first fluorocarbon, and 10% perfluorodecyl bromide, as the second fluorocarbon, emulsified with 3% w/v egg yolk phospholipid. The $LD_{50}$ was approximately 48 ml/kg.

EXAMPLE 6

Stability of Perfluorodecalin/Perfluorodecyl Bromide Emulsions

Concentrated perfluorodecalin emulsions were prepared according to the procedure of Examples 1 and 2 are studied for stability as described in Example 3. Stability data is presented in Table III.

TABLE III

| Stabilizing Effect of Perfluorodecyl Bromide on Concentrated Perfluorodecalin Emulsions | | | | | |
|---|---|---|---|---|---|
| Sample | Initial Size (μm) | Size after 1 month (40° C.) | Size after 2 months (40° C.) | Size after 3 months (40° C.) | S × 1000 ($\mu m^3$/mo) |
| 58.2% w/v FDC 4.6% w/v EYP | 0.17 | 0.33 | 0.40 | 0.49 | 36.6 |
| 58.2% w/v FDC 10% w/v PFDB 4.6% EYP | 0.18 | 0.19 | 0.22 | 0.25 | 3.3 |
| 81% w/v FDC 3% w/v EYP | 0.24 | 0.34 | 0.45 | 0.57 | 56.6 |
| 81% w/v FDC 9% w/v PFDB 3% EYP | 0.19 | 0.22 | 0.25 | 0.27 | 4.3 |

EXAMPLE 7

Predicted Organ Retention Times

Table IV compares physical data (including organ retention times of stabilizing fluorocarbons suggested in the prior art with comparable data for compounds of the present invention. Note that, although the molecular weight and boiling point of F-decylbromide are comparable to the prior art, the critical solution temperature (which is related to organ retention time) is dramatically lower.

Figure 5:
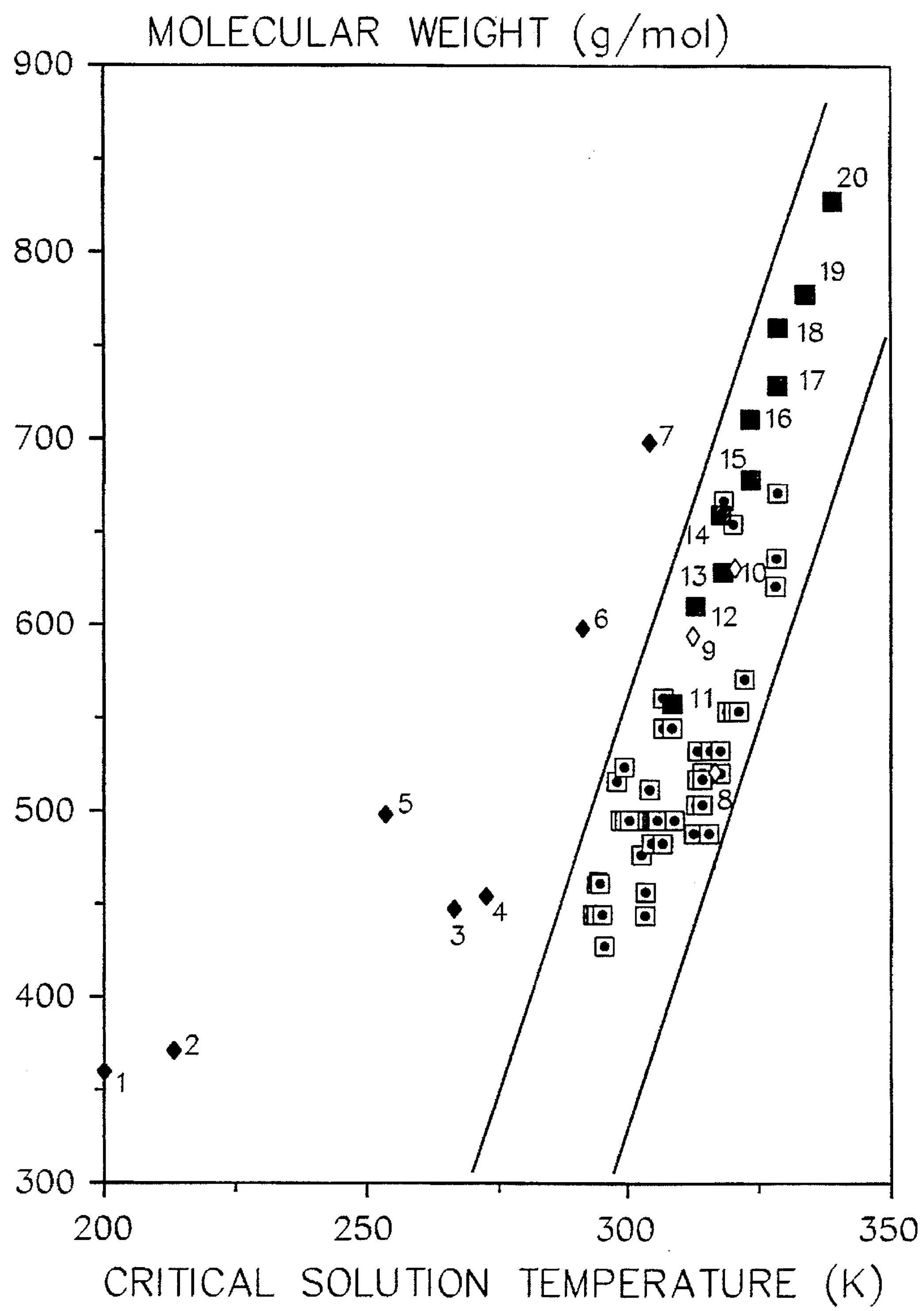
FIG. 5 represents a plot of fluorocarbon molecular weight (g/mol) versus critical solution temperature against hexane (°K.) for various fluorocarbons including the prior art emulsion stabilizers proposed by Davis, Meinert, and Kabalnov.

FIG. 5 illustrates the critical solution temperatures of several fluorocarbons as a function of molecular weight. Note that the prior art stabilizers of Davis, et al., Meinert, Perftoran, and Green Cross (F-tripropylamine), and 50 other assorted fluorocarbons all exhibit a predictable relationship between CST and molecular weight. On the other hand, the lipophilic stabilizers of the present invention have substantially lower CSTs, and therefore substantially shorter organ retention half lives.

TABLE IV

| Physical Properties of Minor Components Discussed in Literature (Proposed Minor Components are listed in Boldface) | | | | | |
|---|---|---|---|---|---|
| Name | Formula | MW(g/mol) | b.p.(C) | CSTH(C) | $t_{1/2}$ (days) |
| | Davis, et al. (U.S. Pat. No. 4,859,363) | | | | |
| F-perhydrofluorene | $C_{13}F_{22}$ | 574 | 192–193 | n.a. | n.a. |
| F-perhydrophenanthrene | $C_{14}F_{24}$ | 624 | 215–216 | 48 | n.a. |
| F-perhydrofluoranthene | $C_{16}F_{26}$ | 686 | 242–243 | n.a. | n.a. |
| | Kabalnov, et al. (Kolloidin Zh. 48:27–32(1986)) | | | | |
| F—N-methylcyclohexylpiperidine | $C_{12}F_{21}N$ | 557 | n.a. | 40 | 60 |
| | Meinert (U.S. Pat. No. 5,120,731) | | | | |
| F—N-cyclohexylmorpholine | $C_{10}F_{18}NO$ | 492 | n.a. | 31 | 13 |
| F-dimorpholinoethane | $C_{10}F_{20}N_2O_2$ | 560 | 164 | 38 | 24 |
| F-dimorpholinopropane | $C_{11}F_{22}N_2O_2$ | 610 | 182 | 45 | 50 |
| F-dimorpholinopentane | $C_{13}F_{26}N_2O_2$ | 710 | 215 | 60 | 280 |
| F-dipiperidine | $C_{10}F_{16}N_2$ | 452 | 145–150 | 36 | 24 |
| F-dipiperidinomethane | $C_{11}F_{18}N_2$ | 502 | 165–175 | 42 | 55 |
| F-dipiperidinoethane | $C_{12}F_{20}N_2$ | 552 | 181–186 | 49 | 124 |
| F-dipiperidinopropane | $C_{13}F_{22}N_2$ | 602 | 195–203 | 56 | 282 |

TABLE IV-continued

Physical Properties of Minor Components Discussed in Literature (Proposed Minor Components are listed in Boldface)

| Name | Formula | MW(g/mol) | b.p.(C) | CSTH(C) | $t_{1/2}$ (days) |
|---|---|---|---|---|---|
| F-dipiperidinobutane | $C_{14}F_{24}N_2$ | 652 | 231–238 | 72 | 1460 |
| Present Study | | | | | |
| F-decalin | $C_{10}F_{18}$ | 462 | 142 | 22 | 7 |
| F-hexyl bromide | $C_6F_{13}Br$ | 399 | n.a. | n.a. | 2 |
| F-octyl bromide | $C_8F_{17}Br$ | 499 | 143 | (−19)[a] | 4 |
| F-decyl bromide | $C_{10}F_{21}Br$ | 599 | (198)[b] | (19)[a] | (18) |
| F-bromopolyether | $C_{11}F_{23}O_3Br$ | 697 | n.a. | 32 | 30 |

[a]values for the critical solution temperature with hexane are estimated from extrapolations linear plots of the critical solution temperature vs. hydrocarbon chain length.
[b]the value of the boiling point of F-decyl bromide is estimated from Hildebrand solution theory.

EXAMPLE 8

Organ Retention Time vs. Fluorocarbon Molecular Weight

FIG. 6 presents data for organ retention times vs. molecular weight for a number of fluorocarbons. The fluorocarbons of Meinert, Kabalnov, and Davis are all contained within the large group, which show a tight correlation between organ retention time and fluorocarbon molecular weight. Based on this the optimal molecular weight for blood substitute applications has been defined to be 460–550 g/mol. The lower limit is defined by fluorocarbons with vapor pressures greater than 20 torr which causes gas emboli, while the upper limit is defined by fluorocarbons with organ retention times of less than 3 weeks. It is clear from FIG. 6 that the lipophilic fluorocarbons PFOB, PFDB, and PPEB (perfluoropolyether bromide, $C_{11}F_{23}O_3Br$) have organ retention times less than be predicted from the molecular weight. Due to their decreased water solubilities (which follows with molecular weight) PFDB and PPEB are expected to stabilize fluorocarbon emulsions by decreasing Ostwald ripening.

EXAMPLE 9

Measurement of Critical Solution Temperature (CST)

Critical solution temperature for fluorocarbon liquids was measured in the following manner: Equivolume mixtures of the test fluorocarbon and hydrocarbon (e.g., hexane) are placed in a sealed vial and submerged in a temperature controlled water bath. Samples are cooled until two distinct phases are present. At this point, the temperature is increased slowly. The lowest temperature at which the two phases are completely miscible (i.e., a single liquid phase) is defined as the CST.

For comparison purposes, all CST temperatures used in this patent are reported versus hexane. It is often not possible, however, to measure the CST for lipophilic fluorocarbons versus hexane, since the CSTs for these substances are very low. Thus, the CST for lipophilic substances is often measured in longer chain length hydrocarbons, and the value versus hexane is determined via extrapolation of linear plots of CST vs. alkane chain length.

Although the present invention has been disclosed in the context of certain preferred embodiments, it is intended that the scope of the invention be measured by the claims that follow, and not be limited to those preferred embodiments.

We claim:

1. A storage stable fluorocarbon emulsion, comprising:

a continuous aqueous phase;

an effective emulsifying amount of an emulsifying agent; and a discontinuous fluorocarbon phase, comprising from about 60% to about 99.9% of one or more first fluorocarbons having a molecular weight from about 448 to about 550 daltons, and from about 0.1% to about 40% of one or more second fluorocarbons having a molecular weight greater than or equal to about 540 daltons, the molecular weight of each second fluorocarbon being greater than each said first fluorocarbon, wherein each said second fluorocarbon is an aliphatic fluorocarbon substituted with at least one lipophilic moiety selected from the group consisting of Br, Cl and I and H.

2. The emulsion of claim 1, wherein said first fluorocarbon is a bis (F-alkyl) ethene.

3. The emulsion of claim 1, wherein said first fluorocarbon is a perfluoroether having the general structure:

$C_nF_{2n+1}$—O—$C_{n'}F_{2n'+1}$, wherein the sum of n and n' equals 6 to 8.

4. The emulsion of claim 1, wherein said first fluorocarbon is perfluoromethylbicyclo [3.3.1]-nonane, perfluorodimethyl bicyclononane, perfluoro-2,2,4,4-tetramethylpentane, perfluorotripropylamine, bis(F-butyl) ethene, (F-isopropyl) (F-hexyl) ethene, perfluoromethyladamantane, perfluorodimethyladamantane, F-N-methyldecahydroisoquinoline, or F-4-methyloctahydroquinolidizine.

5. The emulsion of claim 1, wherein said first fluorocarbon is perfluorooctyl bromide.

6. The emulsion of claim 1, wherein said first fluorocarbon is perfluorodecalin.

7. The emulsion of claim 1, wherein said first fluorocarbon has a half life in vivo of less than about 4 weeks.

8. The emulsion of claim 1, wherein said second fluorocarbon is an aliphatic perfluorocarbon having the general structure:

$C_nF_{2n+1}R$ or $C_nF_{2n}R_2$, wherein n is an integer from 8 to 12 and R is said lipophilic moiety.

9. The emulsion of claim 1, wherein said second fluorocarbon is perfluorododecyl bromide.

10. The emulsion of claim 1, wherein said second fluorocarbon comprises perfluorodecyl bromide.

11. The emulsion of claim 1, wherein said second fluorocarbon comprises a brominated linear or branched perfluoroether having the following general structure:

$C_nF_{2n+1}$—O—$C_{n'}F_{2n'}$Br, wherein n and n' are each at least 2 and the sum of n and n' is greater than or equal to 8.

12. The emulsion of claim 1, wherein each said second fluorocarbon has a critical solution temperature in hexane at least 10° C. lower than that of a fully fluorinated fluorocarbon having substantially the same molecular weight.

13. The emulsion of claim 1, wherein said discontinuous fluorocarbon phase comprises from about 60% to about 99.5% of said first fluorocarbon, and from about 0.5% to about 40% of said second fluorocarbon.

14. The emulsion of claim 1, wherein said discontinuous fluorocarbon phase comprises from about 90% to about 99% of said first fluorocarbon, and from about 1% to about 10% of said second fluorocarbon.

15. The emulsion of claim 1, wherein said emulsifying agent comprises egg yolk phospholipid.

16. The emulsion of claim 1, wherein said effective amount of emulsifying agent comprises 0.1%–10% of egg yolk phospholipid, w/v.

17. The emulsion of claim 1, wherein said emulsifying agent comprises a fluorinated surfactant.

18. A method for imparting particle size stability to a fluorocarbon emulsion having a discontinuous phase of a major amount of one or more first fluorocarbons having a molecular weight from about 460 to about 550 Daltons and a continuous aqueous phase, comprising the step of including in admixture with said first fluorocarbon a minor emulsion-stabilizing amount of one or more second fluorocarbons having a molecular weight greater than said first fluorocarbon wherein each said second fluorocarbon is an aliphatic fluorocarbon substituted with a lipophilic moiety selected from the group consisting of Br, Cl, I and H.

19. The method of claim 18, wherein said first fluorocarbon is a bis (F-alkyl) ethene.

20. The method of claim 18, wherein said first fluorocarbon is a perfluoroether having the general structure:

$C_nF_{2n+1}$—O—$C_{n'}F_{2n'+1}$, wherein the sum of n and n' equals 6 to 10.

21. The method of claim 18, wherein said first fluorocarbon is perfluoromethylbicyclo [3.3.1]-nonane, perfluoro-2, 2,4,4-tetramethylpentane, perfluorotripropylamine, bis(F-butyl)ethene, (F-isopropyl) (F-hexyl) ether, perfluoromethyladamantane, perfluorodimethyladamantane, F-N-methyldecahydroisoquinoline, or F-4-methyloctahydroquinolidizine.

22. The method of claim 18, wherein said first fluorocarbon is perfluorooctyl bromide.

23. The method of claim 18, wherein said first fluorocarbon is perfluorodecalin.

24. The method of claim 18, wherein said first fluorocarbon has a half life in vivo of less than about 4 weeks.

25. The method of claim 18, wherein said second fluorocarbon is an aliphatic perfluorocarbon having the general structure:

$C_nF_{2n+1}R$, wherein n is an integer from 8 to 12 and R is said lipophilic moiety.

26. The method of claim 18, wherein the second fluorocarbon is perfluorododecyl bromide.

27. The method of claim 18, wherein said second fluorocarbon comprises perfluorodecylbromide.

28. The emulsion of claim 18, wherein said second fluorocarbon comprises a brominated linear or branched perfluoroether having the following general structure:

$C_nF_{2n+1}$—O—$C_{n'}F_{2n'}$Br, wherein n and n' are each at least 2 and the sum of n and n' is greater than or equal to 8.

29. The method of claim 18, wherein each said second fluorocarbon has a critical solution temperature in hexane at least 10° C. lower than that of a fully fluorinated fluorocarbon having substantially the same molecular weight.

30. The method of claim 18, wherein said discontinuous fluorocarbon phase comprises from about 60% to about 99.5% of said first fluorocarbon, and from about 0.5% to about 40% of said second fluorocarbon.

31. The method of claim 18, wherein said discontinuous fluorocarbon phase comprises from about 90% to about 99% of said first fluorocarbon, and from about 1% to about 10% of said second fluorocarbon.

32. The method of claim 18, wherein said emulsifying agent comprises egg yolk phospholipid.

33. The method of claim 18, wherein said effective amount of emulsifying agent comprises 0.1%–10% of egg yolk phospholipid, w/v.

34. The method of claim 18, wherein said emulsifying agent comprises a fluorinated surfactant.

* * * * *